United States Patent [19]
de Guillebon

[11] Patent Number: 5,810,879
[45] Date of Patent: Sep. 22, 1998

[54] LAPAROSCOPIC INSTRUMENT

[75] Inventor: Henri F. de Guillebon, Manchester-by-the-Sea, Mass.

[73] Assignee: Microline, Inc., Beverly, Mass.

[21] Appl. No.: 807,897

[22] Filed: Feb. 27, 1997

[51] Int. Cl.⁶ .................................................. A61B 17/00
[52] U.S. Cl. ...................... 606/205; 606/170; 606/174; 600/564
[58] Field of Search .................................. 606/51, 52, 1, 606/170, 171, 174, 180, 205–211; 128/750–755; 600/562–568

[56] References Cited

U.S. PATENT DOCUMENTS

| | | |
|---|---|---|
| 2,518,994 | 8/1950 | Miller . |
| 3,756,242 | 9/1973 | Coss . |
| 4,258,716 | 3/1981 | Sutherland . |
| 4,433,687 | 2/1984 | Burke et al. . |
| 4,674,501 | 6/1987 | Greenberg . |
| 5,308,358 | 5/1994 | Bond et al. .............................. 606/207 |
| 5,358,508 | 10/1994 | Cobb . |
| 5,368,606 | 11/1994 | Marlow et al. . |

*Primary Examiner*—Michael Powell Buiz
*Assistant Examiner*—William Lewis
*Attorney, Agent, or Firm*—Frances P. Craig

[57] ABSTRACT

A laparoscopic instrument assembly for use with a removable tip. The shaft between the removable tip and the external, body or handle portion of the instrument includes a rod moving axially within a sheath to transmit the manipulation of the handle portion to actuate the tip. Both the sheath and the rod are removable from the handle for cleaning of the instrument. Thus, after use, the shaft may be readily disassembled from the handle, the shaft and handle portion sterilized, and the shaft and handle readily reassembled for reuse of the instrument. Alternatively, a non-removable tip may be provided as part of a shaft-tip unit.

13 Claims, 4 Drawing Sheets

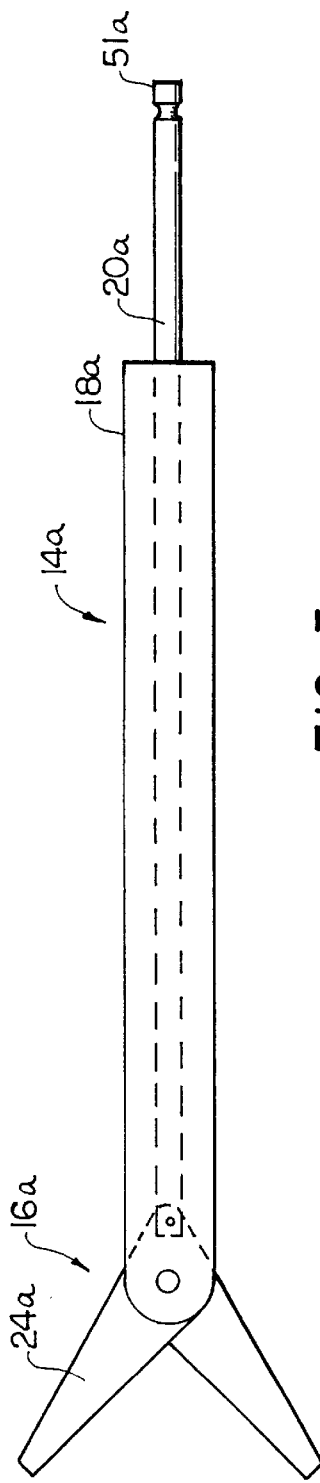
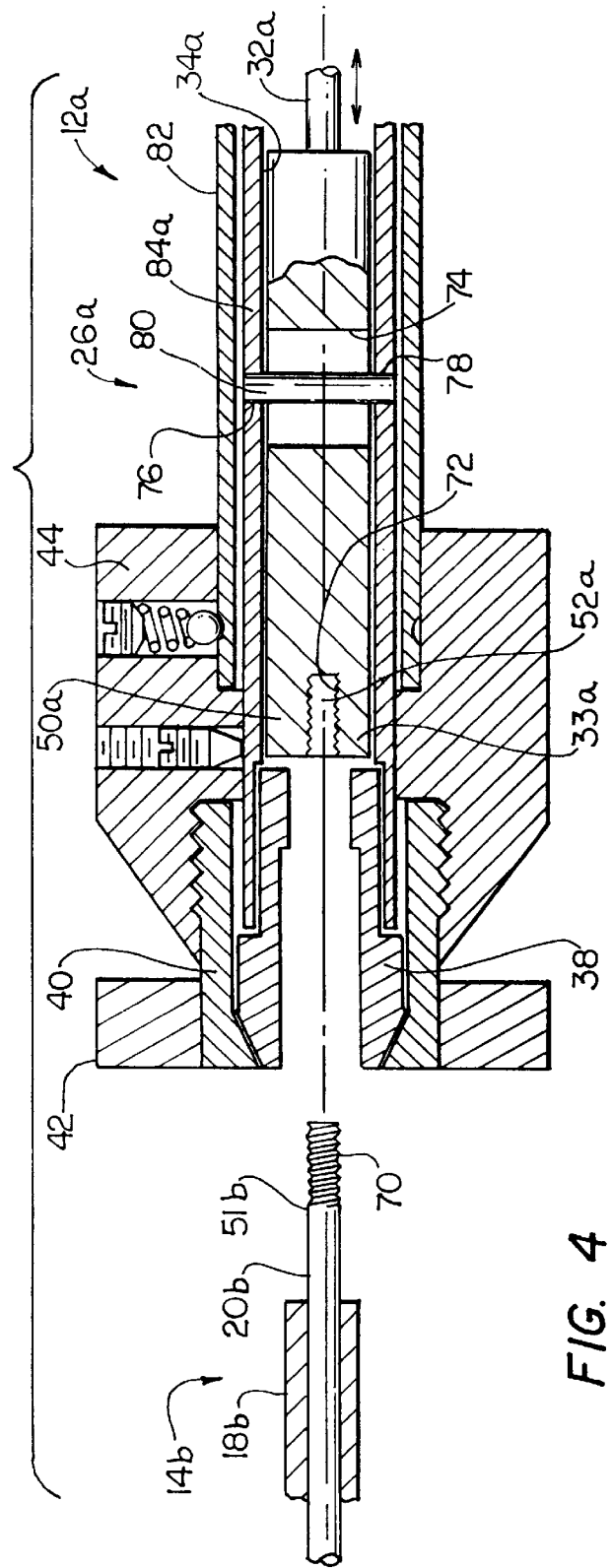

LAPAROSCOPIC INSTRUMENT

CROSS-REFERENCE TO RELATED APPLICATIONS

The present application contains subject matter related to commonly assigned U.S. Pat. No. 5,358,508, incorporated herein by reference.

BACKGROUND OF THE INVENTION

The present invention relates to a laparoscopic instrument, and more particularly to a laparoscopic instrument having a disposable or replaceable, manually operable tip, such as cutting blades, forceps, or the like.

A wide variety of medical instruments for laparoscopic surgery are presently known. Such instruments are used to access, e.g., the peritoneal cavity of a patient through a small incision in the abdominal wall. An endoscope normally is inserted into the cavity through a second incision in the abdominal wall for viewing of the operation of the instrument by the surgeon. Typical of such laparoscopic instruments are those having a tip end including, e.g., cutting blades, forceps, or other surgical device to be inserted into the cavity to perform the surgery, an external end from which the surgeon may manually manipulate the tip device from a position external to the abdominal wall, and an elongated shaft operably connecting the tip end and the external end.

Many such laparoscopic instruments have permanently attached tips. However, a significant advance has been made in the last few years, in that instruments have been developed having disposable tips. Thus, a worn cutting blade may be replaced or one type of tip may be replaced with another, interchangeable type.

Because of the high cost of such laparoscopic instruments, reuse of each instrument would be advantageous in controlling the cost of laparoscopic surgery. However, such reuse requires instruments of rugged construction which may be readily cleaned and sterilized. Known laparoscopic instruments, even those with removable tips, can be difficult to clean due to their length and complex internal structure.

Accordingly, it is an object of the present invention to provide a laparoscopic instrument which overcomes the disadvantages of the prior art.

It is another object of the invention to provide a laparoscopic instrument assembly which is more easily and thoroughly cleaned by normal hospital equipment and procedures.

It is yet another object of the invention to provide a laparoscopic instrument assembly in which the shaft and handle portions of the instrument are readily disassembled for cleaning and reassembled for reuse.

It is still another object of the invention to provide a laparoscopic instrument assembly which includes a disposable shaft, with or without a permanently attached tip.

It is a further object of the invention to provide a laparoscopic instrument assembly in which the tip, shaft, and handle portions of the instrument are readily disassembled and reassembled or replaced for reuse of the instrument.

SUMMARY OF THE INVENTION

In accordance with these objects, the invention is a laparoscopic instrument assembly including a tip having a surgical device or, alternatively, for use with a removable tip. The shaft between the tip and the external, body or handle portion of the instrument includes a rod moving axially within a sheath to transmit the manipulation of the handle portion to actuate the tip. Both the sheath and the rod are removable from the handle for cleaning of the instrument. Thus, after use, the shaft may be readily disassembled from the handle, the shaft and handle portion sterilized, and the shaft and handle readily reassembled for reuse of the instrument. Alternatively, the shaft may be disposed of and the handle portion reassembled with a fresh shaft. The assembly may be used with a removable tip provided separately, or a removable or non-removable tip may be provided as part of the assembly. The removable tip may be cleaned or replaced with a substitute during or after use, or a non-removable tip may be provided as part of a shaft-tip unit.

In one aspect the invention is a laparoscopic instrument assembly. In another aspect, the invention is a laparoscopic instrument assembly for use with a removable tip. The assembly includes a shaft, a manually controllable handle member, and, optionally, a removable or non-removable tip. The shaft includes a tubular sheath and a first rod disposed for axial movement within the sheath. The shaft, the sheath, and the first rod each have a proximal end and a distal end. In one embodiment, the shaft distal end in cludes means for operably and removably attaching a replaceable tip including a surgical device to the shaft for actuation of the surgical device. In another embodiment, the tip is permanently attached to the shaft. The handle member includes a casing having a first axial bore therein and a second rod disposed for axial movement within the first axial bore.

The assembly also includes means for removably attaching the sheath to the casing to extend from the casing with the sheath coaxial with the first axial bore, as well as means for operably and removably attaching the first rod to the second rod for axial movement of the first rod within the sheath in response to movement of the second rod within the first axial bore. On attachment of the removable tip to the shaft distal end, if required, actuation of the surgical device is effected by movement of the second rod within the first axial bore and movement of the first rod within the sheath in response to the movement of the second rod. The shaft and the handle member may readily be disassembled and reassembled for disposal of the shaft and tip or for cleaning and reuse of the laparoscopic instrument assembly.

In a narrower embodiment, the means for operably and removably attaching the first rod to the second rod includes threads on the first rod proximal end and a threaded axial bore in the second rod distal end for mating engagement with one another to removably attach the first rod to the second rod. A pin is inserted through a radial bore in the casing and fits within a slot in the second rod for preventing rotational movement of the second rod while permitting free axial movement of the second rod within a range sufficient to manipulate the tip. The pin is inserted in the casing before actuation of the removable tip, preventing rotational movement of the second rod relative to the first rod, and permitting removal of the first rod from the second rod.

In another narrower embodiment, the first axial bore has a first, larger diameter portion near the first axial bore distal end and a second, smaller diameter portion proximally of the first diameter. The diameter of the second portion is selected for close sliding fit of the second rod therewithin. The first rod proximal end includes an annular groove formed therein. The second rod distal end includes an inwardly extending, second axial bore and one or more radial bores extending from an outer surface thereof to be open to the second axial bore. Each radial bores is of a first, larger diameter at the outer surface and a second, smaller diameter at the second axial bore. The assembly further includes a detent member, e.g., a ball, disposed in each radial bore and engageable with the groove. Each detent member is shaped and sized (a) to permit only partial entry of the detent member into the second axial bore, (b) to be freely movable radially within the radial bore in response to urging from a wall of the first axial bore second portion or from a wall of the groove, and (c) to extend beyond the radial bore either into the second axial bore to engage the groove or into the first axial bore first portion but not into both. Each detent member engages the groove during actuation of the removable tip, preventing removal of the first rod from the second rod. Each detent member is disengageable from the groove when the tip is not actuated, permitting removal of the first rod from the second rod.

BRIEF DESCRIPTION OF THE DRAWINGS

For a better understanding of the present invention, together with other objects, features, advantages, and capabilities thereof, reference is made to the following Description and appended Claims, together with the Drawings in which:

FIG. 3 is an elevation view, partly in section, of the shaft and tip portions of a laparoscopic instrument assembly in accordance with another embodiment of the invention;

FIG. 4 is an exploded elevation view, partly in section, of portions of the shaft and handle member of a laparoscopic instrument assembly in accordance with yet another embodiment of the invention.

DETAILED DESCRIPTION OF THE PREFERRED EMBODIMENTS

Figure 1:
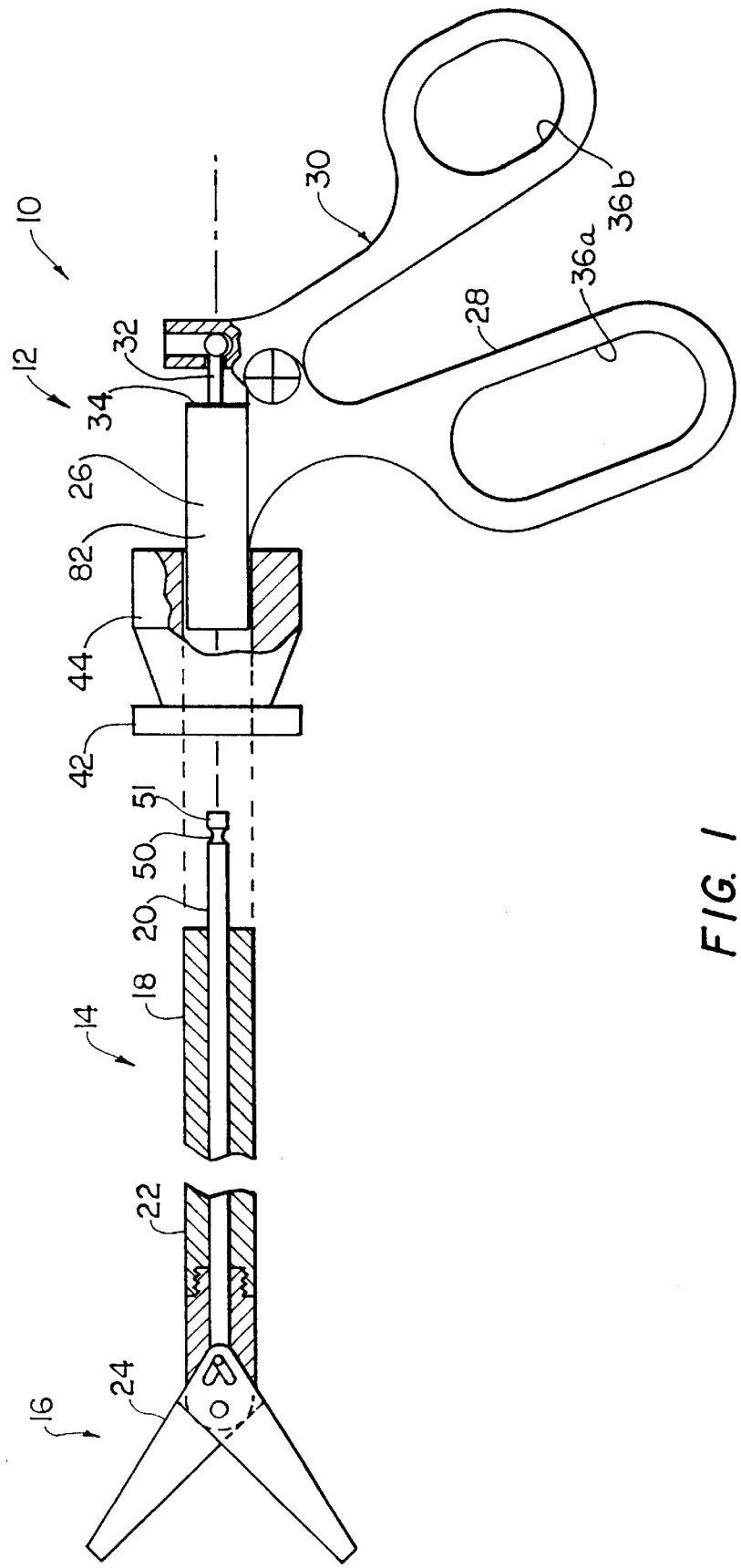
FIG. 1 is an exploded elevation view, partly in section, of a laparoscopic instrument assembly in accordance with one embodiment of the present invention.

The laparoscopic instrument assembly described herein includes a handle member and a shaft operably interconnecting the handle member and a removable or stationary, non-removable tip. The shaft includes a tubular sheath and a rod movable within the sheath. The distal end of the shaft may be operably connected to the tip for actuation of a surgical device on the tip. The proximal end of the shaft is removably and operably connected to the handle member for transmission to the tip surgical device of manipulation by the surgeon of the handle member.

The description below of various embodiments shown in the Drawings refers to laparoscopic instruments in accordance with the invention. However, this description is not intended to limit the scope of the present invention, but merely to be illustrative and representative thereof.

Referring now to FIG. 1, laparoscopic instrument assembly 10 in accordance with one embodiment of the present invention includes handle member 12 and shaft 14 operably interconnecting handle member 12 and removable tip 16. Removable tip 16 may be provided as part of assembly 10 or, alternatively, may be obtained separately. Shaft 14 includes tubular sheath 18 and rod 20 movable within sheath 18. Distal end 22 of shaft 14 is operably connected to tip 16 for actuation of surgical device 24 on tip 16. Handle member 12 includes body, or casing, 26, stationary handle 28, finger-operable, movable handle 30 pivotally linked to stationary handle 28, and rod 32 linked to moveable handle 30 for sliding axial movement within axial bore 34 through casing 26 in response to pivotal movement of movable handle 30. Conveniently, stationary handle 28 and movable handle 30 include openings 36a and 36b shaped to receive fingers and thumb, respectively, of the surgeon for scissors-like manipulation of the instrument.

Figure 2A:
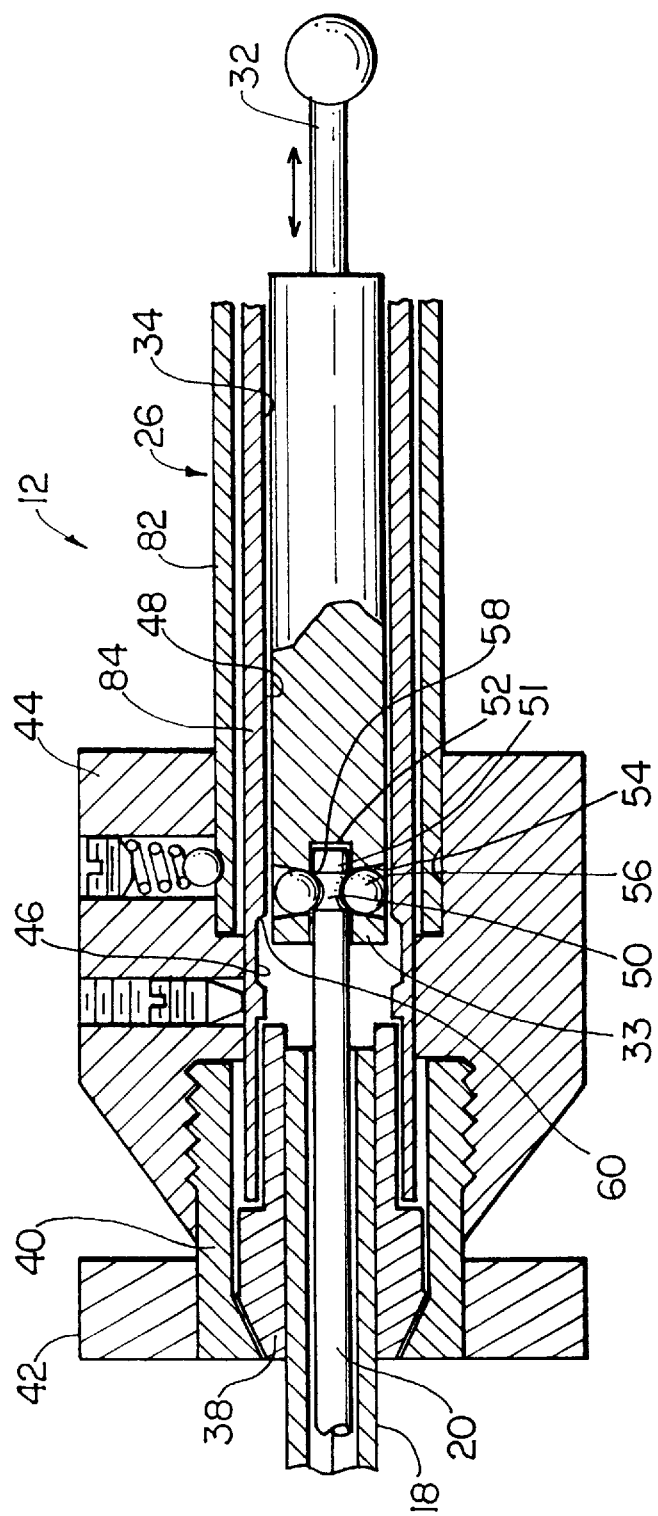
FIGS. 2A and 2B are an elevation views, partly in section, of portions of the shaft and handle member of the assembly of FIG. 1, showing the locking or detent mechanism in further detail.

As shown in FIG. 2A, sheath 18 is attached to casing 26 in a conventional manner using collet 38, collet closer 40 including ring knob 42, and knob 44. Sheath 18 extends distally from casing 26 to be coaxial with bore 34. Rod 20 is operably and removably attached to rod 32 for axial movement of rod 20 within sheath 18 in response to movement of rod 32 within bore 34 in a manner illustrated in further detail in FIGS. 2A and 2B.

Figure 2B:
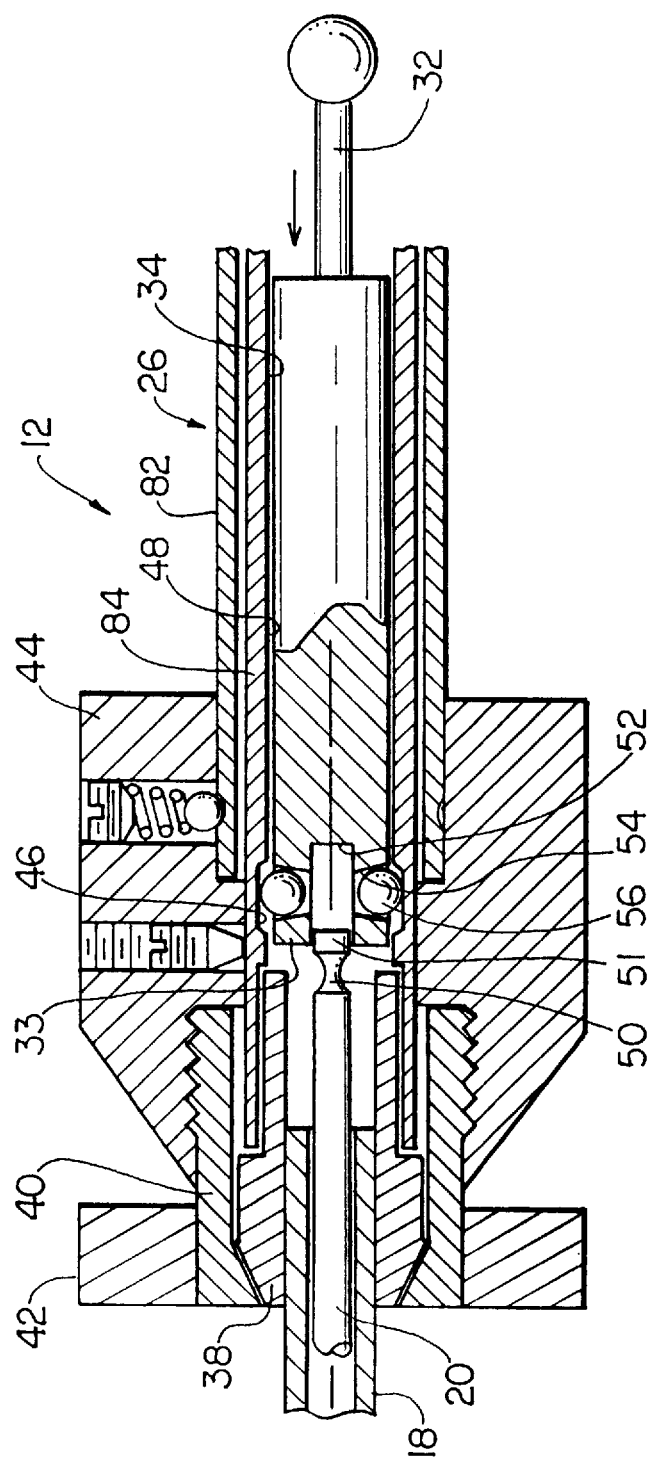

FIGS. 2A and 2B show proximal end 51 of shaft 14 removably and operably connected to handle member 12 for transmission to the tip surgical device of manipulation by the surgeon of handle member 12. Axial bore 34 includes larger diameter portion 46 near the bore distal end and smaller diameter portion 48 proximally of the larger diameter portion. The diameter of narrower portion 48 is selected for close sliding fit of rod 32.

As part of the detent mechanism for attaching rod 20 to rod 32, an annular groove 50 is formed in proximal end 51 of rod 20. Distal end 33 of rod 32 includes axial bore 52 extending inwardly from distal end 33 and sized for close sliding fit of rod 20. Radial bores 54 are also formed in distal end 33 to extend from the outer surface of rod 50 into and open to axial bore 52. The axial position of radial bores 54 is selected for registry of radial bores 54 with groove 50. A radial bore is provided for each detent member, described below. Each radial bore 54 has a larger diameter at the rod outer surface and a smaller diameter where it enters axial bore 52.

Each radial bore 54 contains a detent member 56 therein for mating engagement of detent members 56 with groove 50. The number of detent members 56 is selected to optimize the gripping power of the detent members on rod 20. Typically, from one to six detent members and radial bores are provided, with three the preferred number. Each detent member 56 is shown in the Figures as a ball. However, detent members 56 may be any shape and size which will (a) permit only partial entry of each detent member 56 into axial bore 52; (b) to be freely movable radially within its radial bore 54 in response to urging from the wall of narrow portion 48 of axial bore 34 or from side wall 58 of groove 50; and (c) to extend beyond its radial bore 54 either into axial bore 52 to engage groove 50 or into narrow portion 48 of axial bore 34, but not into both.

Each detent member 56 engages groove 50 during actuation of tip surgical device 24, preventing removal of rod 20 from axial bore 52. However, sheath 18 may be released from casing 26 in a conventional manner, and detent members 56 may be disengaged from groove 50 by separating handles 28 and 30 (FIG. 1) sufficiently wide apart to drive rod 32 distally beyond its operating position, bringing radial bores 54 and detent members 56 in registry with larger portion 46 of axial bore 34. In this position, pulling of shaft 14 forces side wall 58 of groove 50 against detent members 56, forcing the detent members out of groove 50 and into larger portion 46 of axial bore 34, permitting removal of rod 20 from rod 32 and separation of shaft 14 from handle member 12.

For reassembly, e.g., after cleaning, the steps are reversed. With rod 32 in its far distal position, shaft 14 is inserted into handle member 12 with sheath 18 in position within axial bore 34 and rod 20 inserted into axial bore 52 with groove 50 in registry with radial bores 54. Handles 28 and 30 then may be brought closer together, drawing rod 32 in a proximal direction. Wall 60 between larger portion 46 and narrower portion 48 of axial bore 34 then forces detent members 56 out of larger portion 46 of axial bore 34 and into groove 50, locking rod 20 to rod 32. Detent members are held in groove 50 by the close sliding fit of rod 32 within narrower portion 48 of axial bore 34. Ring knob 42 is used in a conventional manner to tighten collet 38 against sheath 18.

For use, removable tip 16 is attached to distal end 22 of shaft 18 in known manner, and surgical device 24, e.g., cutting means or forceps, is actuated by scissor-like movement of handles 28 and 30, which effects axial movement of rod 32 within axial bore 34. Axial movement of rod 32 effects axial movement of rod 20 within and relative to sheath 18, which actuates surgical device 24 in known manner.

FIG. 3 shows an embodiment in which the laparoscopic instrument assembly has a disposable shaft and tip, not intended for reuse. Like features to those shown in FIGS. 1 and 2 are indicated by the same reference numerals. In this embodiment, tip 16a and its surgical device 24a are permanently attached to sheath 18a and rod 20a of shaft 14a in a conventional manner, and are not removable. After use, shaft 14a may be removed from handle member 12, as described above, and disposed of. After cleaning of the handle member, a new shaft with tip may be attached to the handle member, also as described above.

FIG. 4 shows in detail an alternate detent mechanism for operably and removably attaching the shaft to the handle member. Like features to those shown in FIGS. 1, 2, and 3 are indicated by the same reference numerals. Sheath 18b of shaft 14b is attached to casing 26a as described above. Proximal end 51b of rod 20b includes external threads 70 for mating engagement with internal threads 72 in axial bore 52a in rod 32a. Thus, proximal end 51b of rod 20b may be attached to distal end 50a of rod 32a by screwing threads 70 into threads 72.

To permit rotation of rod 20b relative to rod 32a for separation of rods 20b and 32a, while permitting axial movement of rod 32a, rod 32a is provided with slot 74. Radial bore 76 and opposing radial bore 78 are provided in casing 26a to receive and hold in place pin 80. The relative sizes of slot 74 and pin 80 are selected to permit free axial movement of rod 32a within a range sufficient to manipulate a surgical device of a tip attached to shaft 14b. Rotational movement of rod 32a, however, is prevented by pin 80.

Conveniently, as shown in FIGS. 1, 2A, 2B, and 4, casing 26 (FIGS. 2A and 2B) or 26a (FIG. 4) may include ratchet 82 and bearing 84 or 84a, respectively, coaxial with knob 44, to provide axial bore 34 or 34a, respectively. During fabrication of the instrument assembly shown in FIG. 4, pin 80 is inserted into slot 74 of bearing 84, then bearing 84 and pin 80 are inserted into ratchet 82.

Pin 80 remains in place within slot 74 during actuation of a tip surgical device (not shown), preventing rotational movement of rod 32a within bore 34a. The tip and its surgical device may be removable or non-removable from shaft 14b, as described above. Preferably, pin 80 is not fixed within bores 76 and 78, but is retained in place by ratchet 82.

The invention described herein presents to the art a novel, improved laparoscopic instrument assembly having a removable and replaceable or disposable shaft, with or without a permanently attached tip. The replaceable assembly is more easily and thoroughly cleaned by normal hospital equipment and procedures. Alternatively, the shaft may be disposable and readily replaced by a new shaft for reuse of the handle member of the assembly.

While there has been shown and described what are at present considered the preferred embodiments of the invention, it will be apparent to those skilled in the art that modifications and changes can be made therein without departing from the scope of the present invention as defined by the appended Claims.

We claim:

1. A laparoscopic instrument assembly for use with a removable tip, said instrument assembly comprising:

a shaft comprising a tubular sheath and a first rod disposed for axial movement within said sheath, wherein said shaft, said sheath, and said first rod each have a proximal end and a distal end, said shaft distal end including means for operably and removably attaching a replaceable tip including a surgical device to said shaft for actuation of said surgical device;

a manually controllable handle member comprising a casing having a first axial bore therein and a second rod disposed for axial movement within said first bore;

means for removably attaching said sheath to said casing to extend from said casing with said sheath coaxial with said first axial bore; and means for operably and removably attaching said first rod to said second rod for axial movement of said first rod within said sheath in response to movement of said second rod within said first axial bore;

wherein, on attachment of said removable tip to said shaft distal end, actuation of said surgical device is effected by movement of said second rod within said first bore and movement of said first rod within said sheath in response to said movement of said second rod; and wherein said shaft and said handle member may readily be disassembled and reassembled for cleaning and reuse of said laparoscopic instrument assembly.

2. A laparoscopic instrument assembly in accordance with claim 1 wherein said means for operably and removably attaching said first rod to said second rod comprises:

threads on said first rod proximal end and a threaded axial bore in said second rod distal end for mating engagement with one another to removably attach said first rod to said second rod; and a pin inserted through a radial bore in said casing and fitting within a slot in said second rod wherein said pin prevents rotational movement of said second rod within said first axial bore, permits free axial movement of said second rod within a range sufficient to manipulate said tip, and permits removal of said first rod from said second rod.

3. A laparoscopic instrument assembly in accordance with claim 2 wherein said casing includes a knob, a ratchet inserted into, extending from, and coaxial with said knob, and a bearing inserted into and coaxial with said ratchet, said bearing providing said first axial bore, and wherein said casing radial bore extends through opposing sides of said bearing.

4. A laparoscopic instrument assembly in accordance with claim 1 wherein:

said first axial bore has a first, larger diameter portion near said first axial bore distal end and a second, smaller diameter portion proximally of said first diameter, the
diameter of said second portion being selected for close
sliding fit of said second rod therewithin;

said first rod proximal end includes an annular groove
formed therein;

said second rod distal end includes an inwardly extending,
second axial bore and one or more radial bores extending from an outer surface thereof to be open to said
second axial bore, each of said radial bores being of a
first, larger diameter at said outer surface and a second,
smaller diameter at said second axial bore;

and further comprising:
a detent member disposed in each radial bore and
engageable with said groove, wherein each of said
detent members is shaped and sized (a) to permit
only partial entry of said detent member into said
second axial bore, (b) to be freely movable radially
within said radial bore in response to urging from a
wall of said first axial bore second portion or from a
wall of said groove, and (c) to extend beyond said
radial bore either into said second axial bore to
engage said groove or into said first axial bore first
portion but not into both, each of said detent members engaging said groove during actuation of said
removable tip, preventing removal of said first rod
from said second rod, and each of said detent members being disengageable from said groove when
said removable tip is not actuated, permitting
removal of said first rod from said second rod.

5. A laparoscopic instrument assembly in accordance with
claim 4 wherein said one or more radial bores is an annular
array of between three and six radial bores arrayed about the
circumference of said second rod distal end, each containing
a detent member engageable with said groove.

6. A laparoscopic instrument assembly in accordance with
claim 4 wherein said detent member is a ball.

7. A laparoscopic instrument assembly comprising:
a shaft comprising a tubular sheath and a first rod disposed
for axial movement within said sheath, wherein said
shaft, said sheath, and said first rod each have a
proximal end and a distal end;

a tip including a surgical device and having a proximal
end operably attached to said shaft distal end for
actuation of said surgical device;

a manually controlled handle member including a casing
having a first axial bore therein and a second rod
disposed for axial movement within said first axial
bore, wherein said sheath is removably attached to said
casing to extend from said casing with said sheath
coaxial with said first axial bore; and means for operably and removably attaching said first rod
to said second rod for axial movement of said first rod
within said sheath in response to movement of said
second rod within said first axial bore;

wherein actuation of said surgical device is effected by
movement of said second rod within said first axial
bore and movement of said first rod within said sheath
in response to said movement of said second rod; and wherein said shaft and said handle member may readily
be disassembled and reassembled for disposal of said
shaft or for cleaning and reuse of said laparoscopic
instrument assembly.

8. A laparoscopic instrument assembly in accordance with
claim 7 wherein said means for operably and removably
attaching said first rod to said second rod comprises:
threads on said first rod proximal end and on said second
rod distal end for mating engagement with one another
to removably attach said first rod to said second rod;
and a pin inserted through a radial bore in said casing and
fitting within a slot in said second rod, wherein said pin
prevents rotational movement of said second rod, permits free axial movement of said second rod within a
range sufficient to manipulate said tip, and permits
removal of said first rod from said second rod.

9. A laparoscopic instrument assembly in accordance with
claim 8 wherein said casing includes a knob, a ratchet
inserted into, extending from, and coaxial with said knob,
and a bearing inserted into and coaxial with said ratchet, said
bearing providing said first axial bore, and wherein said
casing radial bore extends through diametrically opposite
sides of said bearing.

10. A laparoscopic instrument assembly in accordance
with claim 7 wherein:
said first axial bore has a first, larger diameter portion near
said first axial bore distal end and a second, smaller
diameter portion proximally of said first diameter, the
diameter of said second portion being selected for close
sliding fit of said second rod therewithin;

said first rod proximal end includes an annular groove
formed therein;

said second rod distal end includes an inwardly extending,
second axial bore and one or more radial bores extending from an outer surface thereof to be open to said
second axial bore, each of said radial bores being of a
first, larger diameter at said outer surface and a second,
smaller diameter at said second axial bore;

and further comprising:
a detent member disposed in each radial bore and
engageable with said groove, wherein each of said
detent members is shaped and sized (a) to permit
only partial entry of said detent member into said
second axial bore, (b) to be freely movable radially
within said radial bore in response to urging from a
wall of said first axial bore second portion or from a
wall of said groove, and (c) to extend beyond said
radial bore either into said second axial bore to
engage said groove or into said first axial bore first
portion but not into both, each of said detent members engaging said groove during actuation of said
removable tip, preventing removal of said first rod
from said second rod, and each of said detent members being disengageable from said groove when
said removable tip is not actuated, permitting
removal of said first rod from said second rod.

11. A laparoscopic instrument assembly in accordance
with claim 10 wherein said one or more radial bores is an
annular array of between three and six radial bores arrayed
about the circumference of said second rod distal end, each
containing a detent member engageable with said groove.

12. A laparoscopic instrument assembly in accordance
with claim 10 wherein said detent member is a ball.

13. A laparoscopic instrument assembly in accordance
with claim 7 wherein said tip is a removable tip.

* * * * *